United States Patent [19]

Fiato et al.

[11] Patent Number: 4,719,240

[45] Date of Patent: Jan. 12, 1988

[54] CERIUM PROMOTED FISCHER-TROPSCH CATALYSTS

[75] Inventors: Rocco A. Fiato, Scotch Plains, N.J.; Ronny Bar-Gadda, Palo Alto, Calif.; Sabato Miseo, Pittstown, N.J.

[73] Assignee: Exxon Research and Engineering Company, Florham Park, N.J.

[21] Appl. No.: 927,700

[22] Filed: Nov. 6, 1986

Related U.S. Application Data

[62] Division of Ser. No. 754,004, Jul. 11, 1985, Pat. No. 4,657,885.

[51] Int. Cl.$^4$ .................................................. C07C 1/04
[52] U.S. Cl. ...................................................... 518/717
[58] Field of Search .......................................... 518/717

[56] References Cited

U.S. PATENT DOCUMENTS 2,683,726  7/1954  McGrath ............................. 518/717

Primary Examiner—Howard T. Mars
Attorney, Agent, or Firm—Jay Simon

[57] ABSTRACT

New Fischer-Tropsch catalysts containing a Lanthanide Group element, such as cerium, exhibit improved activity over conventional catalysts and exhibit a reversal in the olefin/paraffin ratio of low molecular weight hydrocarbons. The catalyst comprises:

(a) a Group VIII metal oxide;
(b) a Group IIB metal oxide;
(c) a Group IVB and/or VIIB metal oxide;
(d) a Group IA metal oxide; and,
(e) a Lanthanide group metal oxide.

7 Claims, No Drawings

CERIUM PROMOTED FISCHER-TROPSCH CATALYSTS

This is a division of application Ser. No. 754,004, filed July 11, 1985, U.S. Pat. No. 4,657,885.

BACKGROUND OF THE INVENTION

This invention relates to improved Fischer-Tropsch catalysts containing cerium and their use in $CO/H_2$ hydrocarbon synthesis in which the catalysts display enhanced reactivity and a reversal of olefin/paraffin selectivity versus traditional non-cerium containing F-T catalysts.

The search for processes to provide alternate feedstocks for chemicals, and particularly low molecular weight olefins, has been prompted by the growing shortage of traditional petroleum reserves, as well as the increasing instability of international hydrocarbon sources.

One approach to the problem has been the utilization of the Fischer-Tropsch synthesis in producing a selective product distribution of olefinic hydrocarbons also containing paraffins, in varying olefin/paraffin ratios, depending on the catalyst composition and reaction conditions. Various catalyst combinations of elements have been tested in the past, of which the chief constituent element has been nickel, cobalt, iron or ruthenium. Secondary products in the processes include branched chain hydrocarbons, aliphatic alcohols, aldehydes and acids.

Ruhrchemie Aktiengesellschaft has disclosed in GB 1,512,743, GB 1,553,361, 1,553,362 and 1,553,363, catalysts pertaining to the selective production of $C_2$-$C_4$ olefins from synthesis gas (preferably carbon monoxide and hydrogen). The inventions embody a process for the production of one or more unsaturated hydrocarbons comprising catalytic hydrogenation of a carbon oxide with hydrogen at 250° C. to below 350° C. and a total pressure of 10 to 30 bars in the presence of a catalyst which contains (a) one or more oxides selected from difficult-to-reduce oxides of metals from Group IVB or a lower oxide of Group V and/or Group VII of the Periodic Table; and (b) one or more metals selected from Group VIII of the Periodic Table, the ratio by weight of the metal or metals of the one or more oxides (a) to the one or more metals (b) being in the range 1:2 to 1:10. Additionally, the catalysts can contain Group IA alkali metal and Zn salt promoter agents. In the process, good yields of unsaturated hydrocarbons, especially gaseous olefins, are reported.

U.K. Pat. No. 833,976 discloses a catalyst for the production of ethylene from CO and hydrogen consisting of four components: the first a group including zinc oxides; the second group preferably being cobalt, although iron also could be used, with the proviso that the Group VIII metal component constitutes not more than 10% of the total weight of the catalyst, and being activated by compounds which may include manganese oxide; the third group including an oxide of titanium and/or the rare earth elements; and the fourth group being a carbonate, oxide or hydroxide of an alkali metal. The reaction preferably is conducted at a temperature of from 350° C. to 520° C., preferably from 350° C. to 450° C.

U.K. Pat. No. 506,064 discloses the preparation of an iron-containing Fischer-Tropsch catalyst. The catalyst also may contain minor amounts of alkali compounds which are practically undecomposed up to 1,000° C. This patent also discloses a lengthy list of other compounds that may be added, including titanium, manganese and cerium oxides or hydroxides.

U.S. Pat. No. 4,199,523 discloses a Fischer-Tropsch catalyst containing at least 60% iron. In addition, promoters such as copper and/or silver and alkali are desirable. Other additives, such as alkaline earth metal compounds, zinc oxide, manganese oxide, cerium oxide, vanadium oxide, chromium oxide, and the like may also be used.

U.S. Pat. No. 4,291,126 discloses a catalytic process for the manufacture of linear saturated alcohols from CO and $H_2$. The catalyst comprises copper; cobalt; a third metal selected from chromium, iron, vanadium and manganese; a fourth metal which is a rare earth metal; and a fifth metal which is an alkali metal.

U.S. Pat. No. 4,211,673 discloses a catalyst composed of a rare earth metal, such as cerium, and a transition metal, such as iron, for the reduction of CO to produce oxygenated hydrocarbons.

U.S. Pat. No. 4,186,112 also discloses a Fischer-Tropsch catalyst which may include cerium.

Other patents which disclose the use of cerium include U.S. Pat. Nos. 4,162,234; 4,001,317; 3,992,238; 3,932,551; and 3,615,807.

It is desirable to provide a catalyst and/or process for significantly increasing the activity of a low molecular weight olefin producing catalyst while concurrently maintaining a high olefins product slate under standard olefin producing conditions.

SUMMARY OF THE INVENTION

It has been discovered that a sintered, iron-containing spinel combination metal oxide catalyst containing cerium as a component enhances the catalyst activity and maintains a high olefins/paraffins product distribution during a Fischer-Tropsch alpha olefin synthesis.

It has also been discovered that, under selected conditions of temperature and pressure in conjunction with the catalyst described above, one can also obtain unsaturated hydrocarbons of low molecular weight in good yield. Alternatively, higher molecular weight species may be obtained under suitable conditions.

The catalyst may be prepared by contacting a composition comprising an element or elements from Group VIII, IVB, and/or VIIB, IIB, IA and an element or elements from the lanthanide series. The preparation of the catalyst employed in the process of the invention may be initiated from a variety of precursors. The manner and means of integrating these precursors to a final state of the catalyst may be accomplished utilizing standard practice techniques such as blending, co-precipitating, impregnation, fusion and the like. The following disclosure will illustrate to one skilled in the art several preferred examples of catalyst composition preparation, reactivity, selectivity and activity.

The catalyst comprises about 65 to about 95 weight percent of Group VIII metal oxides such as the oxides of Fe; a Group IVB metal oxide such as $TiO_2$, and/or a Group VIIB metal oxide, such as MnO, ranging from about 10 to about 30 weight percent; a Group IIB metal oxide, such as ZnO, ranging from about 5 to about 20 weight percent; a Group IA metal oxide, such as the oxides of cesium, rubidium, potassium and mixtures thereof ranging from about 1 to about 10 weight percent; and a Lanthanide group metal oxide, such as $CeO_2$, ranging from about 1 to about 10 weight percent.

By this invention, there is provided, a hydrocarbon synthesis catalyst composition comprising a sintered combination of metal oxides having the following components in stated weight percentage of the catalyst composition:

(a) about 5–80 weight percent Fe oxide;
(b) about 4–20 weight percent Zn oxide;
(c) about 10–40 weight percent Ti and/or Mn oxide;
(d) about 1–5 weight percent K, Rb, or Cs oxide or mixtures thereof; and
(e) about 1–10 weight percent Ce oxide.

Where the catalyst contains iron, the catalyst preferably exhibits an X-ray diffraction pattern of an iron-containing spinel or mixture thereof and a Lanthanum group metal oxide, such as cerium oxide. The spinel may comprise magnetite, $Fe_{3-x}Mn_xO_4$, $Fe_{3-x}Zn_xO_4$, $Fe_{3-x}Ti_xO_4$ or mixtures thereof where x ranges between about 0.15 and about 24. The cerium oxide preferably is a homogeneously distributed component, the concentration of the Group IA metal oxide is less than about 2 weight percent of the catalyst composition and the cerium oxide concentration ranges from about 2 to about 5 weight percent of the catalyst composition.

In a preferred embodiment the metal atoms are present in the following generalized and more preferred ratios.

|  | Generalized | More Preferred |
|---|---|---|
| Fe | 0.8–1.2 | 1.0 |
| Zn | 0.05–0.08 | 0.065 |
| Ti and/or Mn | 0.25–0.35 | 0.30 |
| Ce | 0.010–0.15 | 0.030 |
| K, Rb and/or Cs | 0.010–0.15 | 0.030 |

This catalyst composition may be supported on an inert support, such as alumina, silica or magnesia. Further provided is a process for preparing a catalyst composition comprising the steps of:

(a) slurrying an aqueous suspension of oxides of: iron; zinc; titanium and/or manganese; the carbonates of potassium, rubidium, and/or cesium and cerium carbonate;

(b) heating the aqueous slurry to a temperature of at least about 90° C. and;

(c) sintering the resulting solid in an oxygen-containing atmosphere, at a temperature in the range of about 400° C. to about 1200° C. until the X-ray diffraction pattern of the solid is substantially that of at least one iron-containing spinel in the form of $Fe_{3-x}M_xO_4$ where M=Zn, and/or Mn and/or Ti, and x ranges between about 0.15 and about 2.4, in an oxide matrix comprising $CeO_2$.

In a preferred embodiment, the resulting solid is sintered at a temperature of about 100° C. to about 1200° C. for a period of time ranging between about 16 to about 24 hours.

Still further provided is a hydrocarbon synthesis process comprising the steps of:

(a) contacting a feedstream of CO and $H_2$ in a molar ratio in the range from 0.5 to 4.0:1, preferably 0.66 to 2.0:1, more preferably between about 1.0:1.0 and about 2.0:1 with the previously described catalyst at a temperature in the range of about 200° to 350° C., a pressure in the range of about 1 to 50 atmospheres (0.1 to 5 MPaA) preferably between about 5 and about 25 atmospheres and a space velocity in the range of about 10 to 10,000 v/v/hr. preferably between about 500 and about 1500 v/v/hr., thereby producing a hydrocarbon product mixture containing ethylene and ethane, in which the ethylene/ethane molar ratio is greater than one; and, (b) recovering the hydrocarbon product.

DETAILED DESCRIPTION OF THE INVENTION

I. Catalyst Composition

The catalysts of the present invention comprise a sintered combination of metal oxides whose composition, expressed as weight percentage of the catalyst composition for the individual metal oxides is: about 5–80 weight percent Fe oxide as $Fe_2O_3$; about 4–20 weight percent Zn oxide as ZnO; about 10–40 weight percent Ti and/or Mn oxide as $TiO_2$ and/or $MnO_2$; about 1–5 weight percent K,Rb and/or Cs oxide as $K_2O$, $Rb_2O$ and/or CsO; and about 1–10 weight percent Ce oxide as $CeO_2$. The catalyst, after sintering, contains a series of Fe-Zn and Fe-Ti and/or Mn spinels dispersed in an evenly distributed $CeO_2$ matrix.

The Group VIII precursors, preferably Fe containing precursors useful in providing the catalysts of the instant invention include $Fe_2O_3$, $Fe_3O_4$, as well as salts, such as the hydroxide, nitrate, chloride, carbonate, which can be converted to oxides in the high temperature sintering step. A preferred precursor is $Fe_2O_3$. The quantity of the precursor used is adjusted to achieve the desired final composition, after sintering, wherein Fe as the oxide is present at 5–80%, preferably greater than 50%, of the total weight of the final composition.

The Group IIB component, preferably the Zn component of the instant catalyst, can be derived from the oxide, ZnO, or salts, such as the hydroxide, nitrate, chloride or carbonate, which can be converted to the oxide in the high temperature sintering step. The preferred Zn precursor is ZnO. The level of precursor employed is adjusted so the final composition will contain about 4–20 weight percent Zn as the oxide. Zn present in the final composition may be present in that form or in solid solution with Fe oxide as a spinel.

The Group IV component such as Ti and/or the Group VIIB component, such as the Mn component of the instant catalyst, is charged as the oxide, preferably $TiO_2$ or $MnO_2$. These materials are charged at levels such that the final composition will contain them as oxides at 10–40 weight percent levels, although they may be present in the form of solid solutions with the iron-containing component.

The alkali metal Group IA component, preferably K, Rb, Cs or mixtures thereof, is charged as salt, e.g., carbonate, bicarbonate, hydroxide, nitrate, or other salts, which can be converted to oxides, $K_2O$, $Rb_2O$, $Cs_2O$, or mixtures thereof, in the sintering step. These materials are charged such that the final composition will contain about 1–5 weight percent alkali expressed as the oxide, preferably less than 2 weight percent of the final catalyst composition.

The Lanthanum group component, preferably a Ce component of the instant invention, is charged as the oxide or carbonate. These are charged in amounts such that the final composition contains about 1–5 weight percent cerium as the oxide, $CeO_2$, preferably from about 2 to about 5 weight percent of the final catalyst composition.

The catalyst precursor mixture is sintered in air at 800°–1,200° C. X-ray diffraction indicates that $Fe_3O_4$ and a series of iron containing spinels are formed, i.e., $Fe_{3-x}M_xO_4$, where M is Zn, and Ti and/or Mn, and that these components are present in a CeO$_2$ matrix where x ranges between about 0.15 and about 2.4.

Examples of catalyst compositions considered useful in the conversion of CO/H$_2$ to α-olefins include oxide mixtures of Fe/Ti/Zn/Ce/K and Fe/Mn/Zn/Ce/K wherein the metal atom ratios Fe:Ti and/or Mn:Zn:Ce:K are 0.8 to 1.2:0.25 to 0.35:0.05-0.08:0.0-10-0.15:0.010-0.15 and, preferably about, 1.0:0.30:0.065:0.030:0.030, respectively.

The Ce/K metal atom ratio can be varied from about 3/1 to ⅓ while a preferred ratio is about 1/1.

The sintered mixed metal oxide catalysts of this invention are red-brown or red-purple in color, have BET surface areas ≦2m$^2$g, and are highly crystalline in nature as shown by x-ray diffraction. Powder diffraction analysis shows the catalyst to comprise a complex mixture of phases including hematite, magnetite, ilmenite (when TiO$_2$ is present) and a series of mixed spinels Fe$_{3-x}$M$_x$O$_4$ wherein M is Zn and Ti and/or Mn and x ranges between about 0.15 and about 2.4, all in the presence of a discernible CeO$_2$ phase. The combined chemical and physical properties of these catalysts are thought to influence its behavior under CO hydrogenation reaction conditions.

II. Method of Preparation of Composition

The catalysts of this invention are prepared from an aqueous slurry of the precursors, i.e., Fe/Ti or Mn/Zn/Ce/K oxides or salts, which is then placed under vacuum, e.g., 10 mm Hg, at 100° C. to remove excess water. The homogeneous mixture of solids is then sintered in air at a temperature of about 400° C. to about 1,200° C. until X-ray powder diffraction indicates that a stable system has been obtained. The preferred sintering temperature is from about 1,000° to about 1,200° C. and the preferred sintering time is from about 16 to about 24 hours.

III. Olefin Synthesis Process

Prior to their use, catalysts are pretreated with 90% H$_2$ 10% N$_2$ at 250°-600° C., preferably 450°-500° C., at 0.1 to 4 MPaA, preferably 0.5 to 2 MPaA, at flow rates of 10-3,000 v/v catalyst/hr, preferably 100-1,000 v/v catalyst/hr for 1-24 hours, preferably 5-10 hours.

In an olefin synthesis run using the preferred catalyst the temperature may be maintained within the range of about 200° C. to about 350° C., preferably within the range of about 250° C. to about 300° C. The pressure may be maintained within the range of about 0.1 to about 4 MPaA (about 1 to about 40 atmospheres), preferably within the range of about 0.5 to 2.5 MPaA (about 5 to about 25 atmospheres). The space velocity may be maintained within the range of about 10 to about 10,000 volumes of feed per volume of catalyst per hour (v/v/hr), preferably within the range of about 500 to about 1,500 v/v/hr. A fixed bed is preferred, although a fluidized bed and/or a slurry also may be used, since backmixing can be minimized to reduce the residence time and increase selectivity of the primary reaction products. Although upflow of the feed through the bed may function, downflow is preferred since it allows for more efficient removal of liquid products. The CO:H$_2$ molar ratio may be maintained betwen about 0.5:1 and about 4.0:1, with a molar ratio of about 1.0:1.0 and about 2.0:1.0 being preferred. The resulting products primarily comprise C$_2$ to C$_{15}$ compounds in which the olefins comprise approximately 40-70% by weight of the total products. The ethylene to ethane molar ratio preferably will be greater than one.

EXAMPLE 1

Catalyst Preparation

The following metal oxides were mixed in a blender: iron oxide as Fe$_2$O$_3$, TiO$_2$, ZnO, and CeO$_2$ in the following proportions by weight: 1.00:0.30:0.065:0.030 taken as gram-atoms of free metal. After thoroughly mixing, the mixture was sintered by heating at a temperature of about 1050° C. in air for 24 hours, followed by reduction in a H$_2$ atmosphere at about 500° C. for 7 hours.

Hydrocarbon Synthesis Runs

About 5 to 10 grams of the above-prepared catalyst were placed into a stainless steel fixed bed downflow reactor. The catalyst was pretreated by heating at a temperature of 500° C. in a 9:1 H$_2$/N$_2$ atmosphere at a pressure of 100 psia and space velocity of 100 v/v/hr., for 5 to 6 hours. X-ray diffraction analysis showed that not all of the metal oxides were completely reduced. After pretreatment, the catalyst was contacted with a 3:1 H$_2$/CO molar ratio gaseous feedstream at a space velocity of 1737 v/v/hr., a pressure of 394 psia and a temperature of 270° C. for 2-10 hours.

A comparison run was made under substantially the same conditions using a catalyst prepared in accordance with the Example of G.B. Pat. No. 1,512,743, the disclosure of what is incorporated herein by reference, having an average particle size of 1/32", an average surface area of 3 m$^2$/g, and having the composition Fe$_2$O$_3$:TiO$_2$:ZnO:K$_2$O, in a weight ratio of about 1.0:0.3:0.065:0.03, taken as gram-atom ratios of the free metals.

The results for the percent CO conversion as a function of time is given for both catalysts in the following Table I.

TABLE I

| Time On Stream | % CO Conversion | |
|---|---|---|
| Minutes | Fe/Zn/Ti/Ce | Fe/Zn/Ti/K |
| 125 | 48 | — |
| 135 | — | 17 |
| 210 | 49 | — |
| 215 | — | 8 |
| 290 | 54 | — |
| 300 | — | 7 |
| 370 | 58 | — |
| 375 | — | 6 |
| 450 | 62 | — |
| 455 | — | 7 |

As is seen, the cerium-promoted catalyst exhibits an activity difference of about 4- to 5-fold greater than the potassium-promoted catalyst and maintains its catalytic activity over a longer period of time.

The following data in Table II illustrates the product distribution data by carbon number and aliphatic chain type from both runs. Values listed as "1", are between 0 to about 1 percent as measured.

TABLE II

| | Wt. Percent | |
|---|---|---|
| Carbon No. | Fe/Ti/Zn/Ce[a] | Fe/Ti/Zn/K[b] |
| C$_1$ | 35 | 33 |
| C$_2$ | 27 | 14 |
| C$_2$= | 1 | 25 |
| C$_3$ | 1 | 1 |
| C$_3$= | 14 | 1 |

TABLE II-continued

| Carbon No. | Wt. Percent | |
|---|---|---|
| | Fe/Ti/Zn/Ce[a] | Fe/Ti/Zn/K[b] |
| $C_4$ | 5 | 8 |
| $C_4=$ | 8 | 1 |
| $C_5$ | 1 | 1 |
| $C_5=$ | 5 | 11 |
| $C_6$ | 1 | 1 |
| $C_6=$ | 9 | 12 |

[a] Data taken after 134 minutes on-stream.
[b] Data taken after 127 minutes on-stream.

As is seen, olefin/paraffin ratios are substantially higher on the K containing catalyst relative to the Ce containing analog.

EXAMPLE 2

Utilizing the catalysts, procedure and apparatus described in Example 1, following the 3:1 $H_2$:CO run as described in Example 1, the feedstream was changed to 1:1 $H_2$:CO and the hydrocarbon synthesis run was carried out at a temperature of about 270° C., a total pressure of 394 psia, and a space velocity of about 1737 v/v/hr.

The results for both catalysts, expressed in percent CO conversion vs. time, is given below in Table III.

TABLE III

| Time | % CO Conversion | |
|---|---|---|
| (Minutes) | Fe/Ti/Zn/Ce | Fe/Ti/Zn/K |
| 530 | 21 | |
| 610 | 22 | |
| 685 | 23 | |
| 765 | 23 | |
| 845 | 24 | |
| 930 | — | 1 |
| 1015 | — | 1 |
| 1090 | — | 1 |
| 1170 | — | 1 |
| 1250 | — | 1 |

As is seen, operating with a 1:1 $H_2$:CO ratio increases the differential in activity to about twenty-fold between the two catalysts under substantially the same process conditions.

EXAMPLE 3

Catalyst Preparation

The following materials were placed into a blender and mixed for about ½-hour:

| Component | Wt. (Grams) | Gram Atoms Metal | Relative Gram Atoms |
|---|---|---|---|
| $Fe_2O_3$ | 143.0 | 1.79 | 1.000 |
| $Ce_2(CO_3)_3 \cdot 5H_2O$ | 16.5 | 0.06 | 0.030 |
| $TiO_2$ | 41.7 | 0.53 | 0.300 |
| ZnO | 10.0 | 0.12 | 0.065 |

Thirty grams of the resulting mixed solid were placed into a 250 ml. flask. Thirty ml. of distilled water was added and the contents were stirred for one hour, after which the contents were heated, producing a slurry. A mild vacuum was applied to remove water from the slurry, and the resulting solid was dried under 1 mm Hg at 120° C. for 2 hours. The resulting dried material was pulverized, and the vacuum-drying step was repeated for an additional three hours. The solid was pelletized under 20,000 psig and sieved to 20/80 mesh material. The resulting solid Fe/Ti/Zn/Ce was sintered at 1050° C., in air for 16 hours and was subsequently used in hydrocarbon synthesis runs described below.

For comparison purposes, the above-described catalyst preparation procedure was repeated using the following starting materials:

| Component | Weight Grams | Gram Atoms Metal | Relative Gram Atoms |
|---|---|---|---|
| $K_2CO_3$ | 4.14 | 0.06 | 0.030 |
| ZnO | 10.0 | 0.12 | 0.065 |
| $TiO_2$ | 41.7 | 0.53 | 0.300 |
| $Fe_2O_3$ | 143.0 | 1.79 | 1.00 | producing a Fe/Ti/Zn/K (empirical formula) solid.

Hydrocarbon Synthesis Run

A sample comprising 8.3 grams of the Fe/Ti/Zn/Ce solid prepared above was placed into the reactor apparatus described in Example 1 and pretreated by heating in a 9:1 $H_2$:$N_2$ atmosphere at 500° C., 0.77 $MP_aA$ (approximately 115 psia) and 100 v/v catalyst/hr. space velocity for 6 hours.

The run was conducted by contacting the catalyst with a 3:1 $H_2$:CO feedstream at a space velocity of 870 v/v/hr., a pressure of 2.6 $MP_aA$ (approximately 394 psia), and a temperature of 270° C. for 30 hours.

The percent CO conversion as a function of time, and weight percent selectivities of products in terms of carbon numbers, are given below in Tables IV and V, respectively.

As is seen in Table IV, the Ce containing catalyst is more active than the K containing analog.

TABLE IV

| On-Stream Time | % CO Conversion | |
|---|---|---|
| (Minutes) | Fe/Ti/Zn/Ce | Fe/Ti/Zn/K |
| 660 | 55 | — |
| 720 | 53 | — |
| 770 | 54 | — |
| 860 | 54 | — |
| 940 | 55 | — |
| 1420 | — | 21 |
| 1500 | — | 22 |
| 1580 | — | 24 |
| 1670 | — | 26 |
| 1740 | — | 27 |

As is seen in Table V, the Ce containing catalyst generates lower molecular weight products than the K containing analog.

TABLE V

| | Product Selectivities | |
|---|---|---|
| | Wt. % | |
| Carbon No. | Fe/Ti/Zn/Ce | Fe/Ti/Zn/K |
| $C_1$ | 41 | 20 |
| $C_2$ | 31 | 21 |
| $C_3$ | 20 | 22 |
| $C_4$ | 9 | 17 |
| $C_5$ | 7 | 13 |
| $C_6$ | 6 | 3 |
| $C_7$ | 5 | 1 |

EXAMPLE 4

A fifty gram sample of the Fe/Ti/Zn/Ce solid prepared in Example 3, prior to sintering, was placed in a homogenizer and 0.98 g. $K_2CO_3$ was added to produce a solid containing an approximately 1:1 K/Ce atomic ratio and having the following composition:

| Component | Weight Grams | Gram Atoms Metal | Relative Gram Atoms |
|---|---|---|---|
| $Fe_2O_3$ | 143.0 | 1.79 | 1.0 |
| $TiO_2$ | 41.7 | 0.53 | 0.30 |
| ZnO | 10.0 | 0.12 | 0.065 |
| $K_2CO_3$ | 4.14 | 0.06 | 0.030 |
| $Ce(CO_3)_2.5H_2O$ | 16.5 | 0.06 | 0.030 |

The solid was then treated by the "slurry" method as described in Example 3, and subsequently was sintered and pretreated as described in Example 3.

The pretreated catalyst was then contacted with a 1.0:1.0 $H_2$/CO feedstream at a temperature 280° C., a pressure of 2.0 MPaA and a space velocity of 870 v/v/hr. The ethylene product was measured by gas chromatographic analysis over the run and the results given in table VI.

As is seen in Table VI, this catalyst generates a $C_2$-$C_4$ fraction rich in ethylene.

TABLE VI

| % CO conversion | Wt. % Ethylene in $C_2$-$C_4$ Fraction |
|---|---|
| 5 | 60 |
| 15 | 50 |
| 38 | 28 |

EXAMPLE 5

The catalysts prepared in Examples 3 and 4 comprising potassium, cerium, and about a 1.0:1.0 atomic ratio of potassium to cerium were run under substantially the same pretreatment and hydrocarbon synthesis conditions.

The catalysts were pretreated at 500° C., with 9:1 $H_2$:$N_2$ flowstream at a space velocity of about 800 v/v/hr. for about 5 to 6 hours.

The catalysts then were each contacted with a 1:1 $H_2$:CO feedstream, at a pressure of 2.6 MPaA, a space velocity of 870 v/v/hr., and a temperature of 270° C. for a period of 30-50 hours to achieve steady state operation. The percent CO conversion values and product distribution data was collected 5-10 hours after steady state operation was achieved and was analyzed by gas chromatography versus known standards. The results for the three catalysts is listed in Table VII.

TABLE VII

Fischer-Tropsch Performance of Fe/Ti/Zn/M, where M = K, Ce, or K/Ce

| | Catalyst M = | | |
|---|---|---|---|
| | K | Ce | K/Ce |
| | % CO Conversion | | |
| | 2.0 | 17.0 | 24.0 |
| | Wt. % Selectivity | | |
| $CH_4$ | 42 | 24.5 | 14.8 |
| $C_2$= | 19 | 7.5 | 19.7 |
| $C_2$° | 6 | 14.6 | 9.3 |
| $C_3$= | 23 | 6.6 | 12.8 |
| $C_3$° | tr | tr | 2.9 |
| $C_4$+ | 10 | 46.8 | 40.5 |
| $C_2$=/$C_2$° | 3.2 | 0.5 | 2.1 |

EXAMPLE 6

A series of catalysts with a general composition of Fe/Mn/Zn/M, where M=K, Ce, or K/Ce, were prepared by the procedure described in Example 2. The promoters, in quantities listed below, were each added to a mixture of $Fe_2O_3$ (70.5 gm), $MnO_2$ (78.0 gm), and ZnO (5.0 gm).

| M = | K | Ce | K/Ce |
|---|---|---|---|
| $K_2CO_3$ (gm) | 2.94 | 0 | 2.94 |
| $Ce_2(CO_3)_3.5H_2O$ (gm) | 0 | 10.4 | 10.40 |

These catalysts were examined under the Fischer-Tropsch conditions listed in Table VIII. Analysis of the results again shows the synergistic effect of the two promoters to enhance activity and selectivity for the production of low molecular weight olefins.

TABLE VIII

Fischer-Tropsch Performance of Fe/Mn/Zn/M, where M = K, Ce, or K/Ce

| | Catalyst M = | | |
|---|---|---|---|
| | K | Ce | K/Ce |
| | % CO Conversion | | |
| | 18.0 | 62.5 | 54.9 |
| | Wt. % Selectivity | | |
| $CH_4$ | 10.2 | 17.5 | 7.5 |
| $C_2$= | 9.5 | 3.9 | 9.6 |
| $C_2$° | 2.0 | 7.1 | 1.1 |
| $C_3$= | 19.7 | 16.7 | 14.8 |
| $C_3$° | 2.1 | 2.9 | 1.5 |
| $C_4$+ | 56.5 | 51.9 | 65.5 |
| $C_2$=/$C_2$° | 4.8 | 0.6 | 8.7 |

Conditions: 305° C., 2.0 MPa, 1:1 $H_2$:CO, 870 v/v/hr

As is seen, the K/Ce containing catalyst provides high activity, low $CH_4$ selectivity and high $C_2$ and $C_3$ olefin selectivity, i.e., greater productivity of desired and lower productivity of undesired products, such as methane, relative to the potassium or cerium analogs.

EXAMPLE 7

The potassium-cerium promoted catalyst from Example 3 was subjected to pre-reduction with hydrogen at 500° C. for 6.0 hours. The catalyst was then subjected to the reaction conditions shown in Table VIII. The selectivity to $C_2$=-$C_4$= was ≧30% even at high carbon monoxide conversion levels. A slight reduction in $C_2$=-$C_4$= selectivity was noted in systems which employed high (≧3:1) $H_2$:CO feed ratios, as shown in Table IX.

TABLE IX

Evaluation of Fe/Ti/Zn/K/Ce at High Conversion Conditions

| Conditions: | | | |
|---|---|---|---|
| Temp (°C.) | 285° C. | 285° C. | 270° C. |
| Pressure (MPa) | 2.6 | 2.6 | 2.6 |
| $H_2$:CO | 1:1 | 1:1 | 3:1 |
| SHSV (v/v/hr) | 550 | 870 | 550 |
| % CO Conversion | 97 | 85 | 82 |
| Wt. % Selectivity | | | |
| $CH_4$ | 6.0 | 5.8 | 8.7 |
| $C_2$= | 11.3 | 11.4 | 7.3 |
| $C_2$° | 7.6 | 1.9 | 5.7 |
| $C_3$= | 16.5 | 16.4 | 16.0 |
| $C_3$° | tr | tr | 3.5 |
| $C_4$= | 8.9 | 12.5 | 6.8 |
| $C_4$° | 2.5 | 6.4 | 8.9 |
| $C_5$+ | 47.2 | 55.6 | 43.1 |

TABLE IX-continued

Evaluation of Fe/Ti/Zn/K/Ce at High Conversion Conditions

| $C_2^=/C_4^=$ | 36.7 | 40.3 | 30.1 |
| --- | --- | --- | --- |

EXAMPLE 8

A comparative test was conducted of two catalysts having the compositions listed in Table X. The cerium-containing catalyst was prepared by the procedure listed in Example 1. The cupric oxide-containing catalyst was prepared by the procedure described in U.S. Pat. No. 4,199,523, the disclosure of which is incorporated herein by reference. Samples comprising 0.3 grams of each catalyst were placed in a Mettler Thermogravimetric Analyzer and were were heated under flowing hydrogen gas from 25° to 500° C. at a linear temperature ascending rate of 10° C./min., while continuously monitoring the weight loss.

The cerium-containing catalyst lost about 2% of weight upon heating up to 400° C., while the copper-containing catalyst lost above 10% of its weight.

This clearly demonstrates that the replacement of CuO with $CeO_2$ leads to significantly different behavior of the mixed oxide matrix under reducing conditions.

TABLE X

|  | Sample No. 1 Wt. % | Sample No. 2 Wt. % |
| --- | --- | --- |
| $Fe_2O_3$ | 86.0 | 74.40 |
| ZnO | 6.02 | 5.20 |
| $K_2O$ | 1.70 | 4.20 |
| $CeO_2$ | 6.28 | — |
| CuO | — | 16.20 |

What is claimed is:

1. A hydrocarbon synthesis process comprising contacting a feed stream of CO and $H_2$ in a molar ratio of about 0.5 to about 4:1 with a catalyst at a temperature in the range of about 200° to 350° C., a pressure in the range of about 1 to 50 atmospheres, a space velocity in the range of about 10 to 10,000 v/v/hour to produce a hydrocarbon product containing ethylene and ethane in which the ethylene/ethane mole ratio is greater than one, and recovering the product; the catalyst being comprised of a sintered composition containing:
   (a) about 5-80 wt.% Fe oxide,
   (b) about 4-20 wt.% Zn oxide,
   (c) about 10-40 wt.% Ti and/or Mn oxide,
   (d) about 1-5 wt.% of a Group IA metal oxide selected from the group consisting of K, Rb and Cs, and mixtures thereof,
   (e) about 1-10 wt.% Ce oxide such that said sintered combination comprises a series of spinels of Fe, Zn and/or Ti, and/or Mn and said Group I A metal oxide in a Cerium oxide matrix.

2. The process of claim 1 wherein the $H_2$:CO molar ratio is about 1:2 to 2:1.

3. The process of claim 1 wherein the Ce oxide is present as a homogeneously distributed component.

4. The process of claim 1 wherein the Group IA metal oxide is potassium oxide.

5. The process of claim 1 wherein the catalyst is supported on an inert support.

6. The process of claim 5 wherein the support is selected from the group consisting of alumina, silica, and magnesia.

7. The process of claim 1 wherein the metal atoms are present in the following ratios:
   (a) about 0.8-1.2 Fe,
   (b) about 0.05-0.08 Zn,
   (c) about 0.25-0.35 Ti and/or Mn
   (d) about 0.01-0.15 Ce,
   (e) about 0.01-0.15 K.

* * * * *